United States Patent [19]
Mendel

[11] Patent Number: 6,034,105
[45] Date of Patent: Mar. 7, 2000

[54] ALTERATION OF CIRCADIAN RHYTHMICITY WITH A TACHYKININ ANTAGONIST

[75] Inventor: Carl M. Mendel, Short Hills, N.J.

[73] Assignee: Merck & Co., Inc., Rahway, N.J.

[*] Notice: This patent is subject to a terminal disclaimer.

[21] Appl. No.: 09/216,194

[22] Filed: Dec. 18, 1998

Related U.S. Application Data

[63] Continuation of application No. 08/892,076, Jul. 14, 1997, abandoned.

[60] Provisional application No. 60/021,924, Jul. 17, 1996.

[51] Int. Cl.$^7$ .......................... A61K 31/36; C07D 285/04
[52] U.S. Cl. .......................... 514/337; 514/337; 514/364; 514/381; 514/465; 548/253; 548/255
[58] Field of Search .................................. 514/337, 364, 514/381, 465; 548/253, 255

[56] References Cited

U.S. PATENT DOCUMENTS

| | | |
|---|---|---|
| 5,232,929 | 8/1993 | Desai et al. . |
| 5,242,930 | 9/1993 | Baker et al. . |
| 5,321,032 | 6/1994 | Matsuo et al. . |
| 5,538,982 | 7/1996 | Hagan et al. . |
| 5,612,337 | 3/1997 | Baker et al. . |
| 5,719,147 | 2/1998 | Dorn et al. . |
| 5,728,695 | 3/1998 | Harrison et al. . |
| 5,750,549 | 5/1998 | Caldwell et al. ........................ 514/364 |
| 5,877,191 | 3/1999 | Caldwell et al. ........................ 514/337 |

FOREIGN PATENT DOCUMENTS

| | | |
|---|---|---|
| WO 91/12266 | 8/1991 | WIPO . |
| 97/05418 | 6/1997 | WIPO .......................... C07D 491/10 |
| WO 97/49710 | 12/1997 | WIPO . |
| 98/01450 | 1/1998 | WIPO ........................ C07D 491/107 |

OTHER PUBLICATIONS

Hagiwara, et al, *Abstract of PCT Publication WO 91/12266*, 1991.
Shibata, et al, *Brain Research*, 597, 257–263 (1992).
Shibata, et al, *Neuroscience Letters*, 168, 159–162 (1994).
Takatsuji, et al, *Brain Research*, 568, 223–229 (1991).
Abe et al., Substance P receptor . . . , Brain Research vol. 708(1–2) pp. 135–42, 1996.
Shibata et al., Effect of substance P on Circadian rhythms . . . , Brain Research, vol. 597(2) pp. 257–63, 1993.
Mick et al., Marginal topography of neurons . . . , Molecular Brain Res., vol. 21(1–2) pp. 157–161, 1994.

*Primary Examiner*—Keith D. MacMillan
*Assistant Examiner*—Vickie Kim
*Attorney, Agent, or Firm*—J. Eric Thies; David L. Rose

[57] ABSTRACT

A tachykinin antagonist is useful, alone or in conjunction with other agents, for altering circadian rhythmicity and alleviating circadian rhythm disorders and for enhancing and improving the quality of sleep.

20 Claims, No Drawings

ALTERATION OF CIRCADIAN RHYTHMICITY WITH A TACHYKININ ANTAGONIST

CROSS REFERENCE TO RELATED APPLICATIONS

This is a continuation of application Ser. No. 08/892,076 filed Jul. 14, 1997.

This application claims priorty under 35 U.S.C. § 119(e) from U.S. Ser. No. 60/021,924, filed Jul. 17, 1996.

BACKGROUND OF THE INVENTION

Circadian rhythms are exhibited by all eukaryotic plants and animals, including man. Biological rhythms are periodic fluctuations in biological processes over time, including circadian as well as seasonal variations. Circadian, or approximately 24-hour, rhythms include the production of biological molecules such as hormones, the regulation of body temperature, and behavior such as wakefulness, alertness, sleep and periods of activity. Circadian rhythms are endogenous, self-sustained oscillations over 24-hour periods found in organisms ranging from prokaryotes to humans (J S Takahashi, et al. *Science*, 217,1104–1111 (1982)).

In nature, circadian rhythms are closely tied to environmental cues that impose a 24-hour pattern on many of these fluctuations. The regulation of circadian rhythms by signals from the environment involves "entrainment" of the circadian rhythm. The environmental signals which affect entrainment of the circadian rhythm are termed "zeitgebers", an example of which is the light-dark cycle.

The control of many circadian rhythms in mammals is mediated by the portion of the brain called the suprachiasmatic nuclei (SCN). In humans as well as other mammals, the circadian clock, which controls all endogenous circadian rhythms, is located in the SCN of the hypothalamus. Activity, alertness, core body temperature, and many hormones all have endogenous circadian rhythms controlled by the SCN. The SCN is the primary pacemaker for circadian rhythms in mammals. Circadian rhythms are primarily entrained by the light-dark cycle. One of the most important and reproducible characteristics of a circadian clock is that it can respond to exogenous light/dark signals. The circadian clock is composed of three parts: light-input pathways, a clock, and effector pathways. Light signals are conveyed by the retina to the SCN, and the pineal gland produces melatonin (N-acetyl-5-methoxytryptamine), which is regulated by the SCN. Information regarding light is conveyed from the retina to the SCN via the direct retinohypothalamic tract (RHT), as well as indirectly via the lateral geniculate nucleus (LGN).

It has been suggested in the art that excitatory amino acids are involved in the transduction of information regarding the light-dark cycle to the SCN. Acetylcholine, neuropeptide Y, GABA may play a role in the entrainment and/or generation of circadian rhythms in mammals. In addition, $5HT_1$ receptor functioning may play a role in modulating the phase of the SCN clock. Although the primary neurotransmitter of the retinohypothalamic tract is thought to be glutamate, substance P is also present in these fibers.

The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, *Pharmacol. Rev.*, 1983, 35, 85–141). The NK-1 and NK-2 receptor subtypes are implicated in synaptic transmission (Laneuville et al., *Life Sci.*, 42, 1295–1305 (1988)).

Substance P is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence. In addition to SP the known mammalian tachykinins include neurokinin A and neurokinin B. The current nomenclature designates the receptors for SP, neurokinin A, and neurokinin B as neurokinin-1, neurokinin-2, and neurokinin-3, respectively. More specifically, substance P is a neuropeptide that is produced in mammals and possesses a characteristic amino acid sequence.

Substance P is a pharmacologically-active neuropeptide that is produced in mammals and acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al., *Science*, 199, 1359 (1978); P. Oehme et al., *Science*, 208, 305 (1980)) and plays a role in sensory transmission and pain perception (T. M. Jessel, *Advan. Biochem. Psychopharmacol.* 28, 189 (1981)).

Substance P is present in neurons that are part of the circadian clock system, particularly in the SCN, and it may be involved in the transmission of photic information from the retina to the SCN. Substance P increases the firing activity of neurons in the SCN in vitro (Shibata et al, *Brain Research*, 597, 257–263 (1992); Shirakawa, et al, *Brain Research*, 642, 213–220 (1994)) and also increases the locomotor activity of rats (Treptow et al, *Regulatory Peptides*, 5, 343–351 (1983). The fibers of the retinohypothalamic tract are likely to synapse with substance P receptor-containing neurons, which have been identified in the rodent SCN (Takatsuji, et al. *Brain Res.*, 698, 53–61 (1995)). In vitro, substance P has been shown to influence the firing activity and glucose utilization of SCN neurons, as well as to induce phase-shifts in the firing rhythms of SCN neurons (Shirakawa, et al. *Brain Res.*, 642:213–20 (1994); Shibata, et al. *Brain Res.*, 597, 257–63 (1992)). Furthermore, application of substance P to SCN neurons induces expression of the fos protein, which is only induced in response to photic stimulation (Abe, et al. *Brain Res.*, 708,135–42 (1996)). Recent findings indicate that fibers immunoreactive for substance P are also present in the human SCN (Moore, et al. *Brain Res.*, 659, 249–253 (1994); Mai et al. *J. Comparative Neurol.*, 305, 508–25 (1991)). Thus, it is likely that in humans, substance P release from the retinohypothalamic tract is able to convey photic information from the retina to the SCN and influence circadian rhythms. Conversely, a substance P (or neurokinin-1) antagonist may be able to inhibit photic information from reaching the SCN, also influencing the circadian clock and circadian rhythms. The exact role of substance P with respect to circadian rhythms has not been previously determined.

The SCN and the circadian clock control the phases and rhythms of a number of hormonal rhythms in humans. One of the most well-characterized SCN outputs is to the pineal body, via a circuitous route from the hypothalamus to the spinal cord and then back to the pineal. The human pineal gland secretes melatonin in a circadian fashion, such that the plasma concentrations observed during the night are ten to forty times higher than those observed during the day. This plasma melatonin rhythm is a true circadian rhythm, and therefore not dependent upon the exogenous light-dark cycle, as it persists in blinded animals and blind humans. However, light is able to influence the endogenous melatonin rhythm. Light exposure during the night, when plasma melatonin concentrations are high, is able to rapidly suppress plasma melatonin to near daytime levels in a dose-dependent manner (C A Czeisler, et al. *N. Eng. J. Med.*, 332, 6–11 (1995); McIntyre I M, et al. *J Pineal Res*, 6, 149–56 (1989); D B Boivin, et al. *Nature*, 379, 540–2 (1996)). The suppressive effects of light on plasma melatonin concentrations are believed to be mediated through the retina-SCN-pineal neural pathway (R Y Moore, et al. *Science*, 210, 1267–9 (1980)). Thus, because substance P, acting via NK1 receptors, communicates photic information from the retina to the SCN, a neurokinin-1 antagonist will be able to attenuate the effects of light on the SCN, thereby reducing the suppressive effects of light on plasma melatonin concentrations.

Circadian rhythms are also an important modulator of sleep. Although sleep is necessary for survival, its precise homeostatic contribution is unknown. Sleep is not a uniform state, but rather involves several stages characterized by changes in the individual's EEG. A non rapid eye movement (NREM) type (75 to 80% of total sleep time) ranges in depth through stages 1 to 4 (deepest level). Stage 1 sleep is drowsiness, in which the EEG displays a lower voltage, more mixed frequencies and deterioration of alpha rhythm relative to the EEG when the individual is awake. In stage 2, background activity similar to that of stage 1 is experienced, with bursts of slightly higher frequency "sleep spindles" and sporadic higher amplitude slow wave complexes. The third and fourth stages of sleep display increasing high amplitude slow wave activity. The separate sleep stage in which the individual undergoes rapid eye movement (REM) occupies the remainder of the sleep time and occurs 5 to 6 times during a normal nights sleep. REM sleep is characterized by a lower voltage, higher frequency EEG and other characteristics similar to those which occur when the individual is awake, whereas the other four sleep stages are categorized as NREM sleep.

Individuals vary widely in their requirements for sleep, which is influenced by a number of factors including their current emotional state. The natural aging process is associated with changes in a variety of circadian and diurnal rhythms. Age-related changes in the timing and structure of sleep are surprisingly common problems for older people, and are often associated with significant morbidity. With advancing age, the total amount of sleep tends to shorten. Stage 4 can decrease or disappear and sleep may become more fragmented and interrupted. Evaluation of sleep patterns in elderly people shows that the timing of sleep is also phase advanced, especially in women. This tendency to go to sleep and wake up earlier is very frustrating to older people who feel that they are out of step with the rest of the world. In addition, the quality of sleep in the elderly is diminished with a marked reduction in slow wave sleep, a reduction in the deep stages of sleep (especially stage 4), fragmentation of REM sleep and more frequent awakenings. Similarly, non-elderly people may exhibit disturbances in the normal sleep process. These changes in the structure of sleep have been correlated to more frequent napping, decreased daytime alertness and declining intellectual function and cognitive ability. Deprivation of REM sleep has been suggested to interfere with the memory consolidation involved in learning skills through repetitive activity, and slow wave sleep has been implicated as being important in consolidation of events into long term memory. Likewise, decreases in the length of REM stages of sleep may be associated with a decrease in cognitive function and learning, especially diminished retention of memory. Depression and insomnia may involve a disruption of normal circadian rhythmicity.

Sleep disorders generally involve disturbances of sleep, including circadian rhythm disturbances, that affect a subject's ability to fall and/or stay asleep, and involve sleeping too little, too much or resulting in abnormal behavior associated with sleep.

Numerous compounds are employed in the art to facilitate normal sleep and to treat sleep disorders and sleep disturbances, including e.g., sedatives, hypnotics, anxiolytics, antipsychotics, antianxiety agents, minor tranquilizers, melatonin agonists and antagonists, melatonergic agents, benzodiazepines, barbituates, 5HT-2 antagonists, and the like. Similarly, physical methods have been employed to treat patients with sleep disorders such as the use of light therapy or the application of modulated electrical signals to selected nerves or nerve bundles.

Nevertheless, the known threapeutic regimens suffer from numerous problems, including residual effects in daytime function, impairment of memory, potential for addiction, rebound insomnia, "REM rebound" which may be associated with increased dream intensity and the occurrence of nightmares, and the like. Accordingly, a more physiological way to enhance sleep, achieve a chronobiologic (circadian rhythm phase-shifting) effect or alleviate circadian rhythm sleep disorders would be highly desirable.

SUMMARY OF THE INVENTION

The present invention relates to the use of a tachykinin antagonist, in particular a neurokinin-1 receptor antagonist, for achieving a chronobiologic (circadian rhythm phase-shifting) effect and alleviating circadian rhythm disorders in a mammal. The present invention is further directed to the use of a tachyninin antagonist, preferably a neurokinin-1 receptor antagonist, for blocking the phase-shifting effects of light in a mammal. Accordingly, the present invention provides a method for achieving a circadian rhythm phase-shifting effect in a mammal comprising the administration of a tachykinin antagonist, in particular an NK-1 receptor antagonist. The present invention further provides a pharmaceutical composition for achieving a circadian rhythm phase-shifting effect.

The present invention further relates to the use of a tachykinin antagonist, in particular a neurokinin-1 receptor antagonist, for enhancing or improving sleep quality, in particular by increasing sleep efficiency and augmenting sleep maintenance, as well as for preventing and treating sleep disorders and sleep disturbances, in a mammal. Accordingly, the present invention provides a method for enhancing or improving sleep quality and increasing sleep efficiency and sleep iimaintenance in a mammal comprising the administration of a tachykinin antagonist, in particular an NK-1 receptor antagonist. The present invention further provides a pharmaceutical composition for enhancing or improving sleep quality and increasing sleep efficiency and sleep maintenance.

DESCRIPTION OF THE INVENTION

The present invention is directed to the use of a tachyninin antagonist, preferably a neurokinin-1 receptor antagonist, for achieving a chronobiologic (circadian rhythm phase-shifting) effect and alleviating circadian rhythm disorders in a mammal. The present invention is further directed to the use of a tachyninin antagonist, preferably a neurokinin-1 receptor antagonist, for blocking the phase-shifting effects of light in a mammal.

In a preferred embodiment, the present invention provides a method for the phase advance or phase delay in the circadian rhythm of a subject which comprises administering to the subject an appropriate amount of a tachykinin antagonist, in particular an neurokinin-1 receptor antagonist.

The administration to a subject of an appropriate amount of a tachykinin antagonist, in particular an neurokinin-1 receptor antagonist, is useful, for example, in the prevention or treatment of the following conditions to achieve chronobiologic effects and/or to alleviate circadian rhythm phase disturbances: disorders of the sleep-wake schedule; jet lag; shift work; people who have a maladaption to work and off-work schedules; medical residents, nurses, firemen, policemen or those whose duties require alertness and wakefulness ate evening or nighttime hours, or those deprived of sleep for various periods because of their duties or responsiblities; animal workers; athletes who wish to reset their internal clock to a more beneficial time; the infantry, or other members of the armed forces whose duties require extreme levels of alertness and wakefulness, and those who may be sleep deprived in the performance of these duties; submariners, or people confined for research, exploration or industrial purposes below the seas; miners, spelunkers, researchers or those confined beneath the Earth; astronauts in orbit around the Earth, on missions in space to the Earth's moon or to the planets or out of the solar system, or in training for such missions; the blind or sight-impaired or those persons whose ability to distinguish differences in light and dark may be permanently or temporarily impaired; psychiatric patitents; insomniacs; the comatose, or those who need to be maintained in a state of unconsciousness for medical, psychiatric or other reasons; residents of the far North or Antartica, or those persons who live in a climate or climates which possess abnormal amounts of light or darkness; those suffering from seasonal affective disorder (SAD), winter depression, or other forms of depression; the aged; Alzheimer's disease patients, or those suffering from other forms of dementia; patients who require dosages of medication at appropriate times in the circadian cycles; patients suffering from delayed sleep phase syndrome, advanced sleep phase syndrome, or non-24 hr sleep phase syndrome; and patients suffering from primary or secondary insomina or circadian rhythm-related insomnia. The present invention is useful, for example, in the prevention or treatment of conditions associated with circadian rhythmicity as well as mental and physical disorders associated with travel across time zones and with rotating shift-work schedules.

In a preferred embodiment, the present invention provides a method for the prevention or treatment of a circadian rhythm disorder in a mammal, including time-zone change (jet-lag) syndrome, shift-work sleep disorder, delayed sleep-phase syndrome, advanced sleep-phase syndrome, and non-24-hour sleep-wake disorder, which comprises administering to the mammal an effective amount of a tachykinin antagonist.

In another preferred embodiment, the present invention provides a method for shortening the time of reintrainment of circadian rhythms in a subject following a shift in the sleep-wake cycle which comprises administering to the subject an appropriate amount of a tachykinin antagonist, in particular an neurokinin-1 receptor antagonist.

In a more preferred embodiment, the present invention provides a method for alleviating the effects of jet lag in a traveller, especially a mammal, which comprises administering to the traveller an alertness increasing amount of a tachykinin antagonist, in particular an neurokinin-1 receptor antagonist. The purpose of this embodiment is to assist the body to adjust physiologically to the changes in sleep and feeding patterns when crossing several time zones.

In another more preferred embodiment, the present invention provides a method for resetting the internal circadian clock in a subject, for example shift workers changing from a day to a night shift or vice versa, which comprises administering to the subject an appropriate amount of a tachykinin antagonist, in particular an neurokinin-1 receptor antagonist.

The present invention is further directed to the use of a tachyninin antagonist, preferably a neurokinin-1 receptor antagonist, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a tachyninin antagonist. The present invention further provides a pharmaceutical composition for enhancing or improving sleep quality and increasing sleep efficiency and sleep maintenance. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing.

The following outcomes in a subject which are provided by the present invention may be correlated to enhancement in sleep quality: an increase in the value which is calculated from the time that a subject sleeps divided by the time that a subject is attempting to sleep; a decrease in sleep latency (the time it takes to fall asleep); a decrease in the number of awakenings during sleep; a decrease in the time spent awake following the initial onset of sleep; an increase in the total amount of sleep; an increase the amount and percentage of REM sleep; an increase in the duration and occurrence of REM sleep; a reduction in the fragmentation of REM sleep; an increase in the amount and percentage of slow-wave (i.e. stage 3 or 4) sleep; an increase in the amount and percentage of stage 2 sleep; a decrease in the number of awakenings, especially in the early morning; an increase in daytime alertness; and increased sleep maintenance. Secondary outcomes which may be provided by the present invention include enhanced cognitive function and increased memory retention.

The present invention is further useful for the prevention and treatment of sleep disorders and sleep disturbances including sleep problems associated with insomnia, hypersomnia, sleep apnea, narcolepsy, nocturnal myoclonus, REM sleep interruptions, jet-lag, shift workers' sleep disturbances, dysomnias, night terror, insomnias associated with depression or with emotional/mood disorders, dysfunctions associated with sleep (parasomnias), as well as sleep walking and enuresis, as well as sleep disorders which accompany aging. Sleep disorders and sleep disturbances are generally characterized by difficulty in initiating or maintaining sleep or in obtaining restful or enough sleep.

In addition, certain drugs may also cause reductions in REM sleep as a side effect and the present invention may be used to correct those types of sleeping disorders as well. The present invention would also be of benefit in the treatment of syndromes such as fibromyalgia which are manifested by non-restorative sleep and muscle pain or sleep apnea which is associated with respiratory disturbances during sleep. It will be clear to one skilled in the art that the present invention is not limited to just sleep disorders and sleep disturbances, but is applicable to a wide variety of conditions which result from a diminished quality of sleep.

In the present invention, it is preferred that the subject mammal is a human. Although the present invention is applicable both old and young people, it may find greater application in elderly people. Further, although the invention may be employed to enhance the sleep of healthy people, it may be especially beneficial for enhancing the sleep quality of people suffering from sleep disorders or sleep disturbances.

The tachykinin antagonists of use in the present invention may be any tachykinin antagonist known from the art. Preferably, the tachykinin antagonist is an neurokinin-1 or neurokinin-2 receptor antagonist, especially an neurokinin-1 receptor antagonist.

The tachyninin antagonist may be peptidal or non-peptidal in nature, however, the use of a non-peptidal tachykinin antagonist is preferred. In addition, for convenience the use of an orally active tachyninin antagonist is preferred.

In the present invention, it is preferred that the tachyninin antagonist is active upon the central nervous system (CNS), such as the brain, following systemic administration, i.e. that it readily penetrates the CNS. Accordingly, a preferred tachnkinin antagonist for use in the present invention is a CNS-penetrating tachykinin antagonist.

Neurokinin-1 receptor antagonists of use in the present invention are fully described, for example, in U.S. Pat. Nos. 5,162,339, 5,232,929, 5,242,930, 5,373,003, 5,387,595, 5,459,270, 5,494,926, 5,496,833; European Patent Publication Nos. EP 0 360 390, 0 394 989, 0 428 434, 0 429 366, 0 430 771 0 436 334, 0 443 132, 0 482 539, 0 498 069, 0 499 313, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 686 629, 0 699 674, 0 707 006, 0 709 375, 0 709 376; PCT International Patent Publication Nos. WO 90/05525, 90/05729, 91/09844, 91/18899, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 95/02595, 95/06645, 95/07886, 95/07908, 95/08549, 95/14017, 95/15311, 95/16679, 95/17382, 95/18124, 95/18129, 95/22525, 95/30687, 95/23798, 95/33744, 96/05181, 96/05193, 96/07649; and in British Patent Publication Nos. 2 266 529, 2 268 931, 2 269 170, 2 269 590, 2 271 774. Neurokinin-2 receptor antagonists of use in the present invention are described in published European Patent Publication Nos. 0 347 802, 0 428 434, 0 474 561, 0 512 901 and 0 515 240; and in PCT International Patent Publication Nos. WO 92/19254, 93/14084, 94/17045, and 94/29309. The preparation of such compounds is fully described in the aforementioned publications.

A representative first class of tachykinin antagonists is as disclosed in PCT International Patent Publication No. WO 95/16679 as compounds of formula (I):

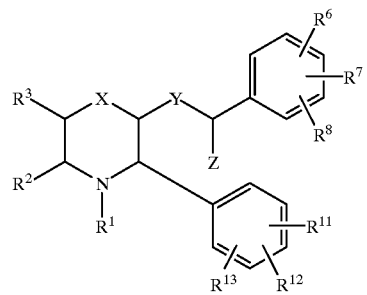

or a pharmaceutically acceptable salt thereof, wherein:
$R^1$ is selected from the group consisting of:
(1) hydrogen;
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo, wherein halo is fluoro, chloro, bromo or iodo,
(h) —$NR^9R^{10}$, wherein $R^9$ and $R^{10}$ are independently selected from:
(i) hydrogen,
(ii) $C_{1-6}$ alkyl,
(iii) hydroxy-$C_{1-6}$ alkyl, and
(iv) phenyl,
(i) —$NR^9COR_{10}$,
(j) —$NR^9CO_2R^{10}$,
(k) —$CONR^9R^{10}$,
(l) —$COR^9$,
(m) —$CO_2R^9$,
(n) heterocycle, wherein the heterocycle is selected from the group consisting of:
(A) benzimidazolyl,
(B) benzofuranyl,
(C) benzothiophenyl,
(D) benzoxazolyl,
(E) furanyl,
(F) imidazolyl,
(G) indolyl,
(H) isooxazolyl,
(I) isothiazolyl,
(J) oxadiazolyl,
(K) oxazolyl,
(L) pyrazinyl,
(M) pyrazolyl,
(N) pyridyl,
(O) pyrimidyl,
(P) pyrrolyl,
(Q) quinolyl,
(R) tetrazolyl,
(S) thiadiazolyl,
(T) thiazolyl, (U) thienyl,
(V) triazolyl,
(W) azetidinyl,
(X) 1,4-dioxanyl,
(Y) hexahydroazepinyl,
(Z) piperazinyl,
(AA) piperidinyl,
(AB) pyrrolidinyl,
(AC) tetrahydrofuranyl, and
(AD) tetrahydrothienyl, and wherein the heterocycle is unsubstituted or substituted with one or more substituent(s) selected from:
(i) $C_{1-6}$ alkyl, unsubstituted or substituted with halo, —$CF_3$, —$OCH_3$, or phenyl,
(ii) $C_{1-6}$ alkoxy,
(iii) oxo,
(iv) hydroxy,
(v) thioxo,
(vi) —$SR^9$,
(vii) halo,
(viii) cyano,
(ix) phenyl,
(x) trifluoromethyl,
(xi) —$(CH_2)_m$—$NR^9R^{10}$, wherein m is 0, 1 or 2,
(xii) —$NR^9COR^{10}$,
(xiii) —$CONR^9R^{10}$,
(xiv) —$CO_2R^9$, and
(xv) —$(CH_2)_m$—$OR^9$;
(3) $C_{2-6}$ alkenyl, unsubstituted or substituted with one or more of the substituent(s) selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$CONR^9R^{10}$,
(i) —$COR^9$,
(j) —$CO_2R^9$,
(k) heterocycle;
(4) $C_{2-6}$ alkynyl;
(5) phenyl, unsubstituted or substituted with one or more of the substituent(s) selected from:
(a) hydroxy,
(b) $C_{1-6}$ alkoxy,
(c) $C_{1-6}$ alkyl,
(d) $C_{2-5}$ alkenyl,
(e) halo,
(f) —CN,
(g) —$NO_2$,
(h) —$CF_3$,
(i) —$(CH_2)_m$—$NR^9R^{10}$,
(j) —$NR^9COR^{10}$,
(k) —$NR^9CO_2R^{10}$,
(l) —$CONR^9R^{10}$,
(m) —$CO_2NR^9R^{10}$,
(n) —$COR^9$,
(o) —$CO_2R^9$;
$R^2$ and $R^3$ are independently selected from the group consisting of:
(1) hydrogen,
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$NR^9R^{10}$,
(i) —$NR^9COR^{10}$,
(j) —$NR^9CO_2R^{10}$,
(k) —$CONR^9R^{10}$,
(l) —$COR^9$, and
(m) —$CO_2R^9$;
(3) $C_{2-6}$ alkenyl, unsubstituted or substituted with one or more of the substituent(s) selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$CONR^9R^{10}$,
(i) —$COR^9$, and
(j) —$CO_2R^9$;
(4) $C_{2-6}$ alkynyl;
(5) phenyl, unsubstituted or substituted with one or more of the substituent(s) selected from:
(a) hydroxy,
(b) $C_{1-6}$ alkoxy,
(c) $C_{1-6}$ alkyl,
(d) $C_{2-5}$ alkenyl,
(e) halo,
(f) —CN,
(g) —$NO_2$,
(h) —$CF_3$,
(i) —$(CH_2)_m$—$NR^9R^{10}$,
(j) —$NR^9COR^{10}$,
(k) —$NR^9CO_2R^{10}$,
(l) —$CONR^9R^{10}$,
(m) —$CO_2NR^9R^{10}$,
(n) —$COR^9$, and
(o) —$CO_2R^9$;
and the groups $R^1$ and $R^2$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) oxazolyl, and
(g) thiazolyl,
and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —$NR^9R^{10}$,
(v) halo, and
(vi) trifluoromethyl;
and the groups $R^2$ and $R^3$ may be joined together to form a carbocyclic ring selected from the group consisting of:
(a) cyclopentyl,
(b) cyclohexyl,
(c) phenyl,
and wherein the carbocyclic ring is unsubstituted or substituted with one or more substituents selected from:
(i) $C_{1-6}$alkyl, (ii) $C_{1-6}$alkoxy,
(iii) —$NR^9R^{10}$,
(iv) halo, and
(v) trifluoromethyl;

and the groups $R^2$ and $R^3$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) furanyl,
(g) oxazolyl,
(h) thienyl, and
(i) thiazolyl, and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —$NR^9R^{10}$,
(v) halo, and
(vi) trifluoromethyl;

$R^6$, $R^7$ and $R^8$ are independently selected from the group consisting of:
(1) hydrogen;
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$NR^9R^{10}$,
(i) —$NR^9COR^{10}$,
(j) —$NR^9CO_2R^{10}$,
(k) —$CONR^9R^{10}$,
(l) —$COR^9$, and (m) —$CO_2R^9$;
(3) $C_{2-6}$ alkenyl, unsubstituted or substituted with one or more of the substituent(s) selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$CONR^9R^{10}$,
(i) —$COR^9$, and
(j) —$CO_2R^9$;
(4) $C_{2-6}$ alkynyl;
(5) phenyl, unsubstituted or substituted with one or more of the substituent(s) selected from:
(a) hydroxy,
(b) $C_{1-6}$ alkoxy,
(c) $C_{1-6}$ alkyl,
(d) $C_{2-5}$ alkenyl,
(e) halo,
(f) —CN,
(g) —$NO_2$,
(h) —$CF_3$,
(i) —$(CH_2)_m$—$NR^9R^{10}$,
(j) —$NR^9COR^{10}$,
(k) —$NR^9CO_2R^{10}$,
(l) —$CONR^9R^{10}$,
(m) —$CO_2NR^9R^{10}$,
(n) —$COR^9$,
(o) —$CO_2R^9$;
(6) halo,
(7) —CN,
(8) —$CF_3$,
(9) —$NO_2$,
(10) —$SR^{14}$, wherein $R^{14}$ is hydrogen or $C_{1-5}$alkyl,
(11) —$SOR^{14}$,
(12) —$SO_2R^{14}$,
(13) $NR^9COR^{10}$,
(14) $CONR^9COR^{10}$,
(15) $NR^9R^{10}$,
(16) $NR^9CO_2R^{10}$,
(17) hydroxy,
(18) $C_{1-6}$alkoxy,
(19) $COR^9$,
(20) $CO_2R^9$,
(21) 2-pyridyl,
(22) 3-pyridyl,
(23) 4-pyridyl,
(24) 5-tetrazolyl,
(25) 2-oxazolyl, and
(26) 2-thiazolyl;

$R^{11}$, $R^{12}$ and $R^{13}$ are independently selected from the definitions of $R^6$, $R^7$ and $R^8$;

X is selected from the group consisting of:
(1) —O—,
(2) —S—,
(3) —SO—, and
(4) —$SO_2$—;

Y is selected from the group consisting of:
(1) a single bond,
(2) —O—,
(3) —S—,
(4) —CO—,
(5) —$CH_2$—,
(6) —$CHR^{15}$—, and
(7) —$CR^{15}R^{16}$—, wherein $R^{15}$ and $R^{16}$ are independently selected from the group consisting of:
(a) $C_{1-6}$ alkyl, unsubstituted or substituted with one or more of the substituents selected from:
(i) hydroxy,
(ii) oxo,
(iii) $C_{1-6}$ alkoxy,
(iv) phenyl-$C_{1-3}$ alkoxy,
(v) phenyl,
(vi) —CN,
(vii) halo,
(viii) —$NR^9R^{10}$,
(ix) —$NR^9COR^{10}$,
(x) —$NR^9CO_2R^{10}$,
(xi) —$CONR^9R^{10}$,
(xii) —$COR^9$, and
(xiii) —$CO_2R^9$;
(b) phenyl, unsubstituted or substituted with one or more of the substituent(s) selected from:
(i) hydroxy, (ii) $C_{1-6}$ alkoxy,
(iii) $C_{1-6}$ alkyl,
(iv) $C_{2-5}$ alkenyl,
(v) halo,
(vi) —CN,
(vii) —$NO_2$,
(viii) —$CF_3$,
(ix) —$(CH_2)_m$—$NR^9R^{10}$,
(x) —$NR^9COR^{10}$,
(xi) —$NR^9CO_2R^{10}$,
(xii) —$CONR^9R^{10}$,
(xiii) —$CO_2NR^9R^{10}$,
(xiv) —$COR^9$, and
(xv) —$CO_2R^9$; and Z is $C_{1-6}$ alkyl.

A particularly preferred compound of formula (I) is 2-(R)-(1-(R)-(3,5-bis(trifluoromethyl)phenyl)ethoxy)-3-(S)-(4-fluorophenyl)-4-(3-(5-oxo-1H,4H-1,2,4-triazolo) methyl-morpholine; or a pharmaceutically acceptable salt thereof.

A representative second class of tachykinin antagonists is as disclosed in PCT International Patent Publication No. WO 95/18124 as compounds of formula (II):

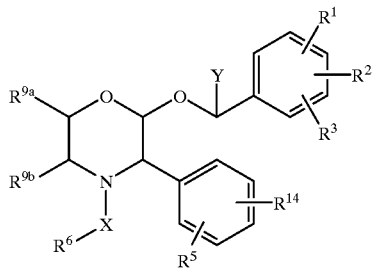

or a pharmaceutically acceptable salt or prodrug thereof, wherein $R^1$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$aLkyl substituted by $C_{1-4}$alkoxy, where $R^a$ and $R^b$ each independently represent hydrogen or $C_{1-4}$alkyl;

$R^2$ is hydrogen, halogen, $C_{1-6}$alkyl, $C_{1-6}$alkoxy substituted by $C_{1-4}$alkoxy or $CF_3$;

$R^3$ is hydrogen, halogen or $CF_3$;

$R^4$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;

$R^5$ is hydrogen, halogen, $C_{1-6}$alkyl, $C_{1-6}$alkoxy substituted by $C_{1-4}$alkoxy or $CF_3$;

$R^6$ is a 5-membered or 6-membered heterocyclic ring containing 2 or 3 nitrogen atoms optionally substituted by =O, =S or a $C_{1-4}$alkyl group, and optionally substituted by a group of the formula $ZNR^7R^8$ where Z is $C_{1-6}$alkylene or $C_{3-6}$cycloalkylene;

$R^7$ is hydrogen, $C_{1-4}$alkyl, $C_{3-7}$cycloalkyl or $C_{3-7}$cycloalkyl$C_{1-4}$alkyl, or $C_{2-4}$alkyl substituted by $C_{1-4}$alkoxy or hydroxyl;

$R^8$ is hydrogen, $C_{1-4}$alkyl, $C_{3-7}$cycloalkyl or $C_{3-7}$cycloalkyl$C_{1-4}$alkyl, or $C_{2-4}$alkyl substituted by one or two substituents selected from $C_{1-4}$alkoxy, hydroxyl or a 4, 5 or 6 membered heteroaliphatic ring containing one or two heteroatoms selected from N, O and S;

or $R^7$, $R^8$ and the nitrogen atom to which they are attached form a heteroaliphatic ring of 4 to 7 ring atoms, optionally substituted by a hydroxy group, and optionally containing a double bond, which ring may optionally contain an oxygen or sulphur ring atom, a group S(O) or $S(O)_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms; or Z, $R^7$ and the nitrogen atom to which they are attached form a heteroaliphatic ring of 4 to 7 ring atoms which may optionally contain an oxygen ring atom;

$R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;

X is an alkylene chain of 1 to 4 carbon atoms optionally substituted by oxo; and Y is a $C_{1-4}$alkyl group optionally substituted by a hydroxyl group; with the proviso that if Y is $C_{1-4}$alkyl, $R^6$ is susbstituted at least by a group of formula $ZNR^7R^8$ as defined above.

A particularly preferred compound of formula (II) is 2-(R)-(1-(R)-(3,5-bis(trifluoromethyl)phenyl)ethoxy)-4-((dimethylaminomethyl)-1,2,3-triazol-4-yl)methyl)-3-(S)-(4-fluorophenyl)morpholine; or a pharmaceutically acceptable salt thereof.

A representative third class of tachykinin antagonists is as disclosed in PCT International Patent Publication No. WO 95/23798 as compounds of formula (III):

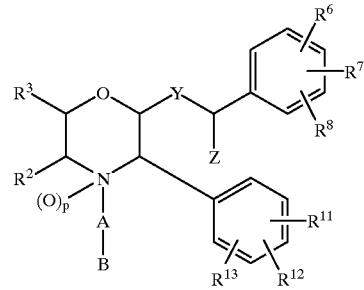

or a pharmaceutically acceptable salt thereof, wherein:

$R^2$ and $R^3$ are independently selected from the group consisting of:
(1) hydrogen,
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$NR^9R^{10}$, wherein $R^9$ and $R^{10}$ are independently selected from:
(i) hydrogen,
(ii) $C_{1-6}$ alkyl,
(iii) hydroxy-$C_{1-6}$ alkyl, and
(iv) phenyl,
(i) —$NR^9COR^{10}$,
(j) —$NR^9CO_2R^{10}$, (k) —CONR⁹R¹⁰,
(l) —COR⁹, and
(m) —CO₂R⁹;
(3) C₂₋₆ alkenyl, unsubstituted or substituted with one or more of the substituent(s) selected from:
(a) hydroxy,
(b) oxo,
(c) C₁₋₆ alkoxy,
(d) phenyl-C₁₋₃ alkoxy,
(e) phenyl,
(f) —CN,
(g) halo,
(h) —CONR⁹R¹⁰,
(i) —COR⁹, and
(j) —CO₂R⁹;
(4) C₂₋₆ alkynyl;
(5) phenyl, unsubstituted or substituted with one or more of the substituent(s) selected from:
(a) hydroxy,
(b) C₁₋₆ alkoxy,
(c) C₁₋₆ alkyl,
(d) C₂₋₅ alkenyl,
(e) halo,
(f) —CN,
(g) —NO₂,
(h) —CF₃,
(i) —(CH₂)ₘ—NR⁹R¹⁰,
(j) —NR⁹COR¹⁰,
(k) —NR⁹CO₂R¹⁰,
(l) —CONR⁹R¹⁰,
(m) —CO₂NR⁹R¹⁰,
(n) —COR⁹, and
(o) —CO₂R⁹;
and, alternatively, the groups R² and R³ are joined together to form a carbocyclic ring selected from the group consisting of:
(a) cyclopentyl,
(b) cyclohexyl,
(c) phenyl,
and wherein the carbocyclic ring is unsubstituted or substituted with one or more substituents selected from:
(i) C₁₋₆alkyl,
(ii) C₁₋₆alkoxy,
(iii) —NR⁹R¹⁰,
(iv) halo, and
v) trifluoromethyl;
and, alternatively, the groups R² and R³ are joined together to form a heterocyclic ring selected from the group consisting of:
(a) pyrrolidinyl,
(b) piperidinyl,
(c) pyrrolyl,
(d) pyridinyl,
(e) imidazolyl,
(f) furanyl,
(g) oxazolyl,
(h) thienyl, and
(i) thiazolyl,
and wherein the heterocyclic ring is unsubstituted or substituted with one or more substituent(s) selected from:
(i) C₁₋₆alkyl,
(ii) oxo,
(iii) C₁₋₆alkoxy,
(iv) —NR⁹R¹⁰,
(v) halo, and
(vi) trifluoromethyl;
R⁶, R⁷ and R⁸ are independently selected from the group consisting of:
(1) hydrogen;
(2) C₁₋₆ alkyl, unsubstituted or substituted with one or more of the substituents selected from:
(a) hydroxy,
(b) oxo,
(c) C₁₋₆ alkoxy,
(d) phenyl-C₁₋₃ alkoxy,
(e) phenyl,
(f) —CN,
(g) halo,
(h) —NR⁹R¹⁰,
(i) —NR⁹COR¹⁰,
(j) —NR⁹CO₂R¹⁰,
(k) —CONR⁹R¹⁰,
(l) —COR⁹, and
(m) —CO₂R⁹;
(3) C₂₋₆ alkenyl, unsubstituted or substituted with one or more of the substituent(s) selected from:
(a) hydroxy,
(b) oxo,
(c) C₁₋₆ alkoxy,
(d) phenyl-C₁₋₃ alkoxy,
(e) phenyl,
(f) —CN,
(g) halo,
(h) —CONR⁹R¹⁰,
(i) —COR⁹, and
(j) —CO₂R⁹;
(4) C₂₋₆ alkynyl;
(5) phenyl, unsubstituted or substituted with one or more of the substituent(s) selected from:
(a) hydroxy,
(b) C₁₋₆ alkoxy,
(c) C₁₋₆ alkyl,
(d) C₂₋₅ alkenyl,
(e) halo,
(f) —CN,
(g) —NO₂,
(h) —CF₃,
(i) —(CH₂)ₘ—NR⁹RI1,
(j) —NR⁹COR¹⁰,
(k) —NR⁹CO₂R¹⁰,
(l) —CONR⁹R¹⁰,
(m) —CO₂NR⁹R¹⁰,
(n) —COR⁹, and
(o) —CO₂R⁹;
(6) halo,
(7) —CN,
(8) —CF₃,
(9) —NO₂,
(10) —SR¹⁴, wherein R¹⁴ is hydrogen or C₁₋₅alkyl,
(11) —SOR¹⁴,
(12) —SO₂R¹⁴,
(13) NR⁹COR¹⁰,
(14) CONR⁹COR¹⁰,
(15) NR⁹R¹⁰,
(16) NR⁹CO₂R¹⁰,
(17) hydroxy,
(18) C₁₋₆alkoxy,
(19) COR⁹,

(20) $CO_2R^9$,
(21) 2-pyridyl,
(22) 3-pyridyl,
(23) 4-pyridyl,
(24) 5-tetrazolyl,
(25) 2-oxazolyl, and
(26) 2-thiazolyl;

$R^{11}$, $R^{12}$ and $R^{13}$ are independently selected from the definitions of $R^6$, $R^7$ and $R^8$, or —OX;

A is selected from the group consisting of:

(1) $C_{1-6}$ alkyl, unsubstituted or substituted with one or more of the substituents selected from:
   (a) hydroxy,
   (b) oxo,
   (c) $C_{1-6}$ alkoxy,
   (d) phenyl-$C_{1-3}$ alkoxy,
   (e) phenyl,
   (f) —CN,
   (g) halo,
   (h) —$NR^9R^{10}$,
   (i) —$NR^9COR^{10}$,
   td) —$NR^9CO_2R^{10}$,
   (k) —$CONR^9R^{10}$,
   (l) —$COR^9$, and
   (m) —$CO_2R^9$;

(2) $C_{2-6}$ alkenyl, unsubstituted or substituted with one or more of the substituent(s) selected from:
   (a) hydroxy,
   (b) oxo,
   (c) $C_{1-6}$ aLkoxy,
   (d) phenyl-$C_{1-3}$ alkoxy,
   (e) phenyl,
   (f) —CN,
   (g) halo,
   (h) —$CONR^9R^{10}$,
   (i) —$COR^9$, and
   (j) —$CO_2R^9$; and (3) $C_{2-6}$ alkynyl;

B is a heterocycle, wherein the heterocycle is selected from the group consisting of:

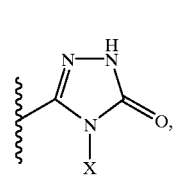
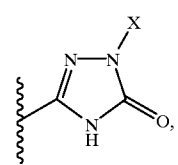

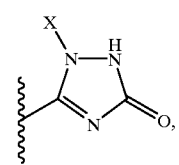
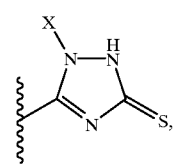

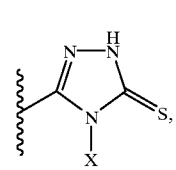
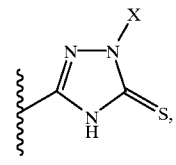

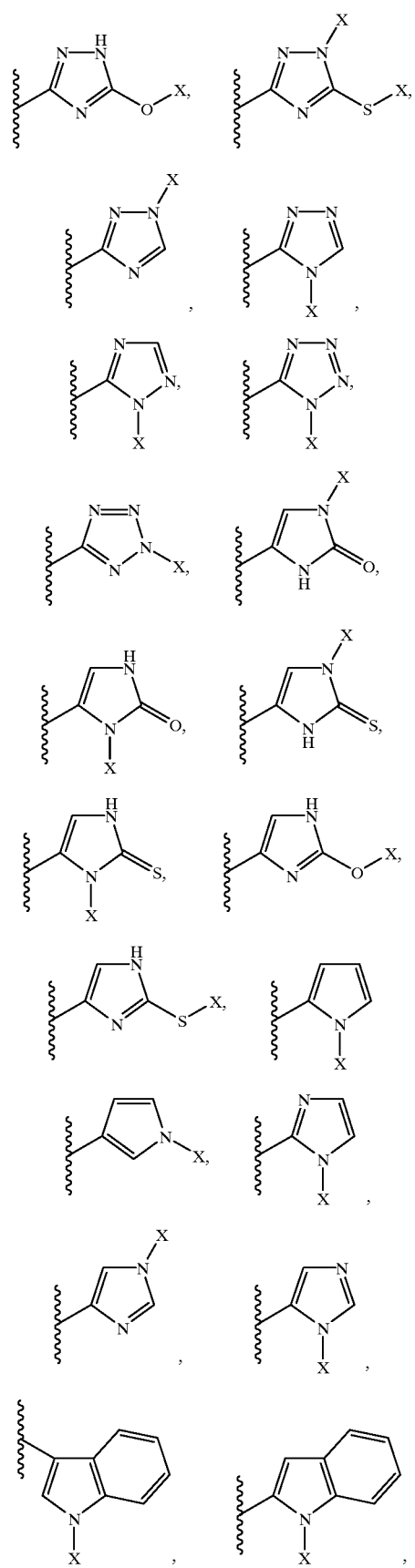

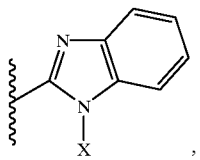

and wherein the heterocycle is substituted in addition to —X with one or more substituent(s) selected from:
(i) hydrogen;
(ii) $C_{1-6}$ alkyl, unsubstituted or substituted with halo, —$CF_3$, —$OCH_3$, or phenyl,
(iii) $C_{1-6}$ alkoxy,
(iv) oxo,
(v) hydroxy,
(vi) thioxo,
(vii) —$SR^9$,
(viii) halo,
(ix) cyano,
(x) phenyl,
(xi) trifluoromethyl,
(xii) —$(CH_2)_m$—$NR^9R^{10}$, wherein m is 0, 1 or 2,
(xiii) —$NR^9COR^{10}$,
(xiv) —$CONR^9R^{10}$,
(xv) —$CO_2R^9$, and
(xvi) —$(CH_2)_m$—$OR^9$;

p is 0 or 1;

X is selected from:

(a) —PO(OH)O—•$M^+$, wherein $M^+$ is a pharmaceutically acceptable monovalent counterion,
(b) —PO($O^-$)$_2$•2$M^+$,
(c) —PO($O^-$)$_2$•$D^{2+}$, wherein $D^{2+}$ is a pharmaceutically acceptable divalent counterion,
(d) —CH($R^4$)—PO(OH)O—•$M^+$, wherein $R^4$ is hydrogen or $C_{1-3}$ alkyl,
(e) —CH($R^4$)—PO($O^-$)$_2$•2$M^+$,
(f) —CH($R^4$)—PO($O^-$)$_2$•$D^{2+}$,
(g) —$SO_3$—•$M+$,
(h) —CH($R^4$)—$SO_3$—•$M^+$,
(i) —CO—$CH_2CH_2$—$CO_2$—•$M^+$,
(j) —CH($CH_3$)—O—CO—$R^5$, wherein $R^5$ is selected from the group consisting of:

(i)
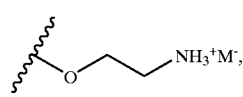

(ii)
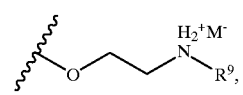

(iii)
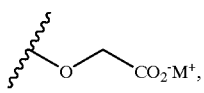

(iv)
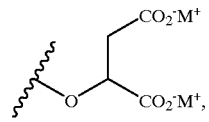

(v)
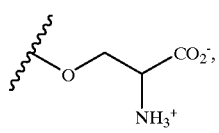

(vi)
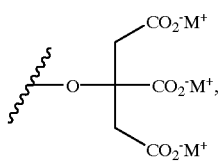

(vii)
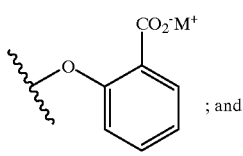
; and (k) hydrogen, with the proviso that if p is 0 and none of $R^{11}$, $R^{12}$ or $R^{13}$ are —OX, then X is other than hydrogen;

Y is selected from the group consisting of:
(1) a single bond,
(2) —O—,
(3) —S—,
(4) —CO—,
(5) —$CH_2$—,
(6) —$CHR^{15}$—, and
(7) —$CR^{15}R^{16}$—, wherein $R^{15}$ and $R^{16}$ are independently selected from the group consisting of:
  (a) $C_{1-6}$ alkyl, unsubstituted or substituted with one or more of the substituents selected from:
    (i) hydroxy,
    (ii) oxo,
    (iii) $C_{1-6}$ alkoxy,
    (iv) phenyl-$C_{1-3}$ alkoxy,
    (v) phenyl,
    (vi) —CN,
    (vii) halo,
    (viii) —$NR^9R^{10}$,
    (ix) —$NR^9COR^{10}$,
    (x) —$NR^9CO_2R^{10}$,
    (xi) —$CONR^9R^{10}$,
    (xii) —$COR^9$, and
    (xiii) —$CO_2R^9$;
  (b) phenyl, unsubstituted or substituted with one or more of the substituent(s) selected from:
    (i) hydroxy,
    (ii) $C_{1-6}$ alkoxy,
    (iii) $C_{1-6}$ alkyl,
    (iv) $C_{2-5}$ alkenyl,
    (v) halo,
    (vi) —CN,
    (vii) —$NO_2$,
    (viii) —$CF_3$, (ix) —(CH$_2$)$_m$—NR$^9$R$^{10}$,
(x) —NR$^9$COR$^{10}$,
(xi) —NR$^9$CO$_2$R$^{10}$,
(xii) —CONR$^9$R$^{10}$,
(xiii) —CO$_2$NR$^9$R$^{10}$,
(xiv) —COR$^9$, and
(xv) —CO$_2$R$^9$;

Z is selected from:
(1) hydrogen,
(2) C$_{1-6}$ alkyl, and
(3) hydroxy, with the proviso that if Y is —O—, Z is other than hydroxy, or if Y is —CHR$^{15}$—, then Z and R$^{15}$ are optionally joined together to form a double bond.

A particularly preferred compound of formula (III) is 2-(R)-(1-(R)-(3,5-bis(trifluoromethyl)phenyl)ethoxy)-3-(S)-(4-fluoro)-phenyl-4-(3-(1-monophosphoryl-5-oxo-1H-1,2,4-triazolo)methyl)morpholine, or a pharmaceutically acceptable salt thereof. In particular, the bis(N-methyl-D-glucamine) salt is preferred.

A representative fourth class of tachykinin antagonists is as disclosed in European Patent Publication No. 0 436 334 as compounds of formula (IV):

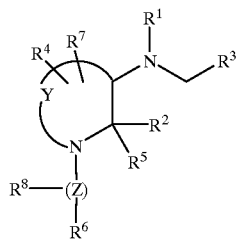

or a pharmaceutically acceptable salt thereof, wherein
Y is (CH$_2$)$_n$ wherein n is an integer from 1 to 4, and wherein any one of the carbon-carbon single bonds in said (CH$_2$)n may optionally be replaced by a carbon-carbon double bond, and wherein any one of the carbon atoms of said (CH$_2$)n may optionally be substituted with R$^4$, and wherein any one of the carbon atoms of said (CH$_2$)$_n$ may optionally be substituted with R$^7$;

Z is (CH$_2$)m wherein m is an integer from 0 to 6, and wherein any one of the carbon-carbon single bonds of (CH$_2$)$_m$ may optionally be replaced by a carbon-carbon double bond or a carbon-carbon triple bond, and any one of the carbon atoms of said (CH$_2$)$_m$ may optionally be substituted with R$^8$;

R$^1$ is hydrogen or C$_{1-8}$alkyl optionally substituted with hydroxy, C$_{1-4}$alkoxy or fluoro;

R$^2$ is a radical selected from hydrogen, C$_{1-6}$ straight or branched alkyl, C$_{3-7}$cycloalkyl wherein one of the CH2 groups in said cycloalkyl may optionally be replaced by NH, oxygen or sulphur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl-C$_{2-6}$alkyl, benzhydryl and benzyl, wherein each of said aryl and heteroaryl groups and the phenyl moieties of said benzyl, phenyl-C$_{2-6}$allyl and benzhydryl may optionally be substituted with one or more substituents independently selected from halo, nitro, C$_{1-6}$alkyl, C$_{1-6}$alkoxy, trifluoromethyl, amino, C$_{1-6}$alkylamino, C$_{1-6}$alkyl-O-CO, C$_{1-6}$alkyl-O-CO-C$_{1-6}$alkyl, C$_{1-6}$alkyl-CO-O, C$_{1-6}$alkyl-CO-C$_{1-6}$alkyl-O-, C$_{1-6}$alkyl-CO, C$_{1-6}$alkyl-CO-C$_{1-6}$alkyl-, di-C$_{1-6}$alkylamino, —CONH-C$_{1-6}$alkyl, C$_{1-6}$alkyl-CO-NH-C$_{1-6}$alkyl, —NHCOH and —NHCO-C$_{1-6}$alkyl; and wherein one of the phenyl moieties of said benzhydryl may optionally be replaced by naphthyl, thienyl, furyl or pyridyl;

R$^5$ is hydrogen, phenyl or C$_{1-6}$alkyl;
or R$^2$ and R$^5$ together with the carbon to which they are attached, form a saturated ring having from 3 to 7 carbon atoms wherein one of the CH$_2$ groups in said ring may optionally be replaced by oxygen, NH or sulfur;

R$^3$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of the (CH$_2$) groups in said cycloalkyl may optionally be replaced by NH, oxygen or sulphur;

wherein each of said aryl and heteroaryl groups may optionally be substituted with one or more substituents, and said C$_{3-7}$cycloalkyl may optionally be substituted with one or two substituents, each of said substituents being independently selected from halo, nitro, C$_{1-6}$alkyl, C$_{1-6}$alkoxy, trifluoromethyl, amino, C$_{1-6}$alkylamino, —CO-NH-C$_{1-6}$alkyl, C$_{1-6}$alkyl-CO-NH-C$_{1-6}$alkyl, —NHCOH and —NH CO-C$_{1-6}$alkyl;

R$^4$ and R$^7$ are each independently selected from hydroxy, halogen, halo, amino, oxo, cyano, methylene, hydroxymethyl, halomethyl, C$_{1-6}$alkylamino, di-C$_{1-6}$alkylamino, C$_{1-6}$alkoxy, C$_{1-6}$alkyl-O-CO, C$_{1-6}$alkyl-O-CO-C$_{1-6}$alkyl, C$_{1-6}$alkyl-CO-O, C$_{1-6}$alkyl-CO-C$_{1-6}$alkyl-O-, C$_{1-6}$alkyl-CO-, C$_{1-6}$alkyl-CO-C$_{1-6}$alkyl, and the radicals set forth in the definition of R$^2$;

R$^6$ is —NHCOR$^9$, —NHCH$_2$R$^9$, SO$_2$R$^8$ or one of the radicals set forth in any of the definitions of R$^2$, R$^4$ and R$^7$;

R$^8$ is oximino (═NOH) or one of the radicals set forth in any of the definitions of R$^2$, R$^4$ and R$^7$;

R$^9$ is C$_{1-6}$alkyl, hydrogen, phenyl or phenylC$_{1-6}$alkyl; with the proviso that (a) when m is 0, R$^8$ is absent, (b) when R$^4$, R$^6$, R$^7$ or R$^8$ is as defined in R$^2$, it cannot form together with the carbon to which it is attached, a ring with R$^5$, and (c) when R$^4$ and R$^7$ are attached to the same carbon atom, then either each of R$^4$ and R$^7$ is independently selected from hydrogen, fluoro and C$_{1-6}$alkyl, or R$^4$ and R$^7$, together with the carbon to which they are attached, for a C$_{3-6}$ saturated carbocyclic ring that forms a spiro compound with the nitrogen-containing ring to which they are attached.

A particularly preferred compound of formula (IV) is (2S,3S)-cis-3-(2-methoxybenzylamino)-2-phenylpiperidine; or a pharmaceutically acceptable salt thereof.

A representative fifth class of tachykinin antagonists is as disclosed in PCT International Patent Publication No. WO 93/21155 as compounds of formula (V):

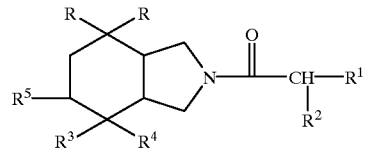

or a pharmaceutically acceptable salt thereof, wherein
radicals R are phenyl radicals optionally 2- or 3-substituted by a halogen atom or a methyl radical;

R¹ is optionally substituted phenyl, cyclohexadienyl, naphthyl, indenyl or optionally substituted heterocycle;

R² is H, halogen, OH, alkyl, aminoalkyl, alkylaminoalkyl, dialkylaminoalkyl, alkyloxy, alkylthio, acyloxy, carboxy, optionally substituted alkyloxycarbonyl, benzyloxycarbonyl, amino or acylamino;

R³ is optionally 2-substituted phenyl;

R⁴ is OH or fluorine when R⁵ is H;

or R⁴ and R⁵ are OH;

or R⁴ and R⁵ together form a bond.

A particularly preferred compound of formula (V) is (3aS,4S,7aS)-7,7-diphenyl-4-(2-methoxyphenyl)-2-[(2S)-(2-methoxyphenyl)propionyl]perhydroisoindol-4-ol; or a pharmaceutically acceptable salt thereof.

A representative sixth class of tachykinin antagonists is as disclosed in European Patent Publication No. 0 591 040 as compounds of formula (VI):

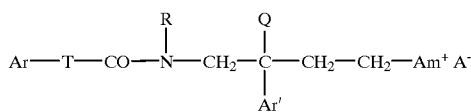

wherein

Ar represents an optionally substituted mono-, di- or tricyclic aromatic or heteroaromatic group;

T represents a bond, a hydroxymethylene group, a $C_{1-4}$alkoxymethylene group or a $C_{1-5}$alkylene group;

Ar' represents a phenyl group which is unsubstituted or substituted by one or more substituents selected from halogen, preferably chlorine or fluorine, trifluoromethyl, $C_{1-4}$alkoxy, $C_{1-4}$alkyl where the said substituents may be the same or different; a thienyl group; a benzothienyl group; a naphthyl group; or an indolyl group;

R represents hydrogen, $C_{1-4}$alkyl, —$C_{1-4}$alkoxy$C_{1-4}$alkyl, or —$C_{2-4}$alkanoyloxy$C_{2-4}$alkyl;

Q represents hydrogen;

or Q and R together form a 1,2-ethylene, 1,3-propylene or 1,4-butylene group;

Am⁺ represents the radical

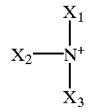

in which $X_1$, $X_2$ and $X_3$, together with the nitrogen atom to which they are attached, form an azabicyclic or azatricyclic ring system optionally substituted by a phenyl or benzyl group; and A⁻ represents a pharmaceutically acceptable anion.

A particularly preferred compound of formula (VI) is (+)-1-[2-[3-(3,4-dichlorophenyl)-1-[(3-isopropoxyphenyl)acetyl]-3-piperidinyl]ethyl]-4-phenyl-1-azabicyclo[2,2,2]octane; or a pharmaceutically acceptable salt, especially the chloride, thereof A representative seventh class of tachykinin antagonists is as disclosed in European Patent Publication No. 0 532 456 as compounds of formula (VII):

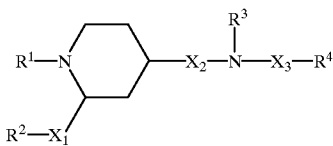

or a pharmaceutically acceptable salt thereof, wherein

R¹ represents an optionally substituted aralkyl, aryloxyalykl, heteroaralkyl, aroyl, heteroaroyl, cycloalkylcarbonyl, aralka noyl, heteroarylalkanoyl, aralkoxycarbonyl or arylcarbamoyl group or the acyl group of an (-amino acid optionally N-substituted by a lower alkanoyl or carbamoyl-lower alkanoyl group;

R² represents cycloalkyl or an optionally substituted aryl or heteroaryl group;

R³ represents hydrogen, alkyl, carbamoyl or an alkanoyl or alkenoyl group optionally substituted by carboxy or esterified or amidated carboxy;

R⁴ represents an optionally substituted aryl group or an optionally partially saturated heteroaryl group;

$X_1$ represents methylene, ethylene, a bond, an optionally ketalised carbonyl group or an optionally etherified hydroxymethylene group;

$X_2$ represents alkylene, carbonyl or a bond; and $X_3$ represents carbonyl, oxo-lower alkyl, oxo(aza)-lower alkyl, or an alkyl group optionally substituted by phenyl, hydroxymethyl, optionally esterified or amidated carboxy, or (in other than the (-position) hydroxy.

A particularly preferred compound of formula (VII) is (2R* ,4S *)-2-benzyl-1-(3,5-dimethylbenzoyl)-N-(4-quinolinylmethyl)-4-piperidineamine; or a pharmaceutically acceptable salt thereof.

A representative eighth class of tachykinin antagonists is as disclosed in European Patent Publication No. 0 443 132 as compounds of formula (VIII):

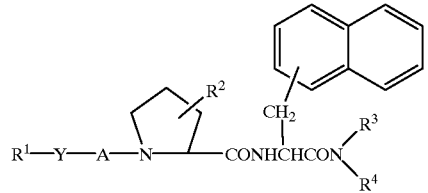

or a pharmaceutically acceptable salt thereof, wherein
wherein R¹ is aryl, or a group of the formula:

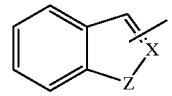

or a pharmaceutically acceptable salt thereof, wherein

X is CH or N; and

Z is O or N-R⁵, in which R⁵ is hydrogen or lower alkyl;

R² is hydroxy or lower alkoxy;

R³ is hydrogen or optionally substituted lower alkyl;

R⁴ is optionally substituted ar(lower)alkyl;

A is carbonyl or sulfonyl; and

Y is a bond or lower alkenylene.

A particularly preferred compound of formula (VIII) is the compound of formula (VIIIa)

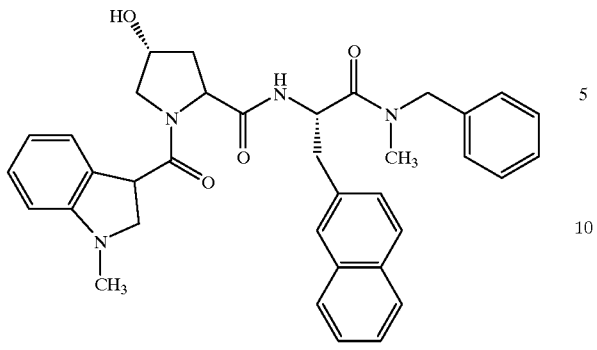
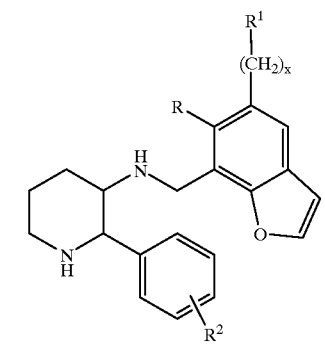

A representative ninth class of tachykinin antagonists is as disclosed in PCT International Patent Publication No. WO 95/08549 as compounds of formula (IX):

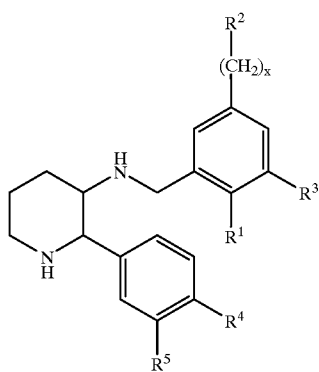

wherein $R^1$ is a $C_{1-4}$alkoxy group;
$R^2$ is

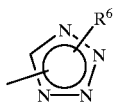

$R^3$ is a hydrogen or halogen atom;
$R^4$ and $R^5$ may each independently represent a hydrogen or halogen atom, or a $C_{1-4}$ alkyl, $C_{1-4}$ alkoxy or trifluoromethyl group;
$R^6$ is a hydrogen atom, a $C_{1-4}$ alkyl, $(CH_2)_m$ cyclopropyl, $-S(O)_nC_{1-4}$ alkyl, phenyl, $NR^7R^8$, $CH_2C(O)CF_3$ or trifluoromethyl group;
$R^7$ and $R^8$ may each independently represent a hydrogen atom, or a $C_{1-4}$ alkyl or acyl group;
x represents zero or 1;
n represents zero, 1 or 2;
m represents zero or 1;
and pharmaceutically acceptable salts and solvates thereof.

A particularly preferred compound of formula (IX) is [2-methoxy-5-(5-trifluoromethyl-tetrazol-1-yl)-benzyl]-(2S-phenyl-piperidin-3S-yl)-amine; or a pharmaceutically acceptable salt thereof.

A representative tenth class of tachykinin antagonists is as disclosed in PCT International Patent Publication No. WO 95/06645 as compounds of formula (IX):

wherein
R represents a hydrogen atom or a $C_{1-4}$ alkoxy group;
$R^1$ is selected from phenyl, optionally substituted by a group $-(CH_2)_nCONR^3R^4$ or $S(O)_mR^3$; or a 5- or 6-membered aromatic heterocycle containing 1, 2, 3 or 4 heteroatoms selected from oxygen, nitrogen, or sulphur, optionally substituted by a $C_{1-4}$ alkyl, trifluoromethyl or cyano group or a group $-(CH_2)_nCONR^3R^4$;
$R^2$ represents a hydrogen or halogen atom;
$R^3$ and $R^4$ independently represent hydrogen or $C_{1-4}$ alkyl;
n represents zero, 1 or 2;
m represents zero, 1 or 2;
z represents zero or 1;
and pharmaceutically acceptable salts and solvates thereof.

A particularly preferred compound of formula (X) is [5-(5-methyl-tetrazol-1-yl)-benzofuran-7-ylmethyl]-(2S-phenyl-piperidin-3S-yl)-amine; or a pharmaceutically acceptable salt thereof.

The preparation of the foregoing compounds is fully described in the referenced patents and publications.

Unless otherwise defined herein, suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl, n-butyl, sec-butyl and tertbutyl.

Unless otherwise defined herein, suitable alkenyl groups include straight-chained and branched alkenyl groups containing from 2 to 6 carbon atoms. Typical examples include vinyl and allyl groups.

Unless otherwise defined herein, suitable alkynyl groups include straight-chained and branched alkynyl groups containing from 2 to 6 carbon atoms. Typical examples include ethynyl and propargyl groups.

Unless otherwise defined herein, suitable cycloalkyl groups include groups containing from 3 to 7 carbon atoms. Particular cycloalkyl groups are cyclopropyl and cyclohexyl.

Unless otherwise defined herein, suitable aryl groups include phenyl and naphthyl groups. A particular aryl-$C_{1-6}$alkyl, e.g. phenyl-$C_{1-6}$alkyl, group is benzyl.

Unless otherwise defined herein, suitable heteroaryl groups include pyridyl, quinolyl, isoquinolyl, pyridazinyl, pyrimidinyl, pyrazinyl, pyranyl, furyl, benzofuiryl, thienyl, benzthienyl, imidazolyl, oxadiazolyl and thiadiazolyl groups.

The term "halogen" as used herein includes fluorine, chlorine, bromine and iodine. The compounds of use in this invention may have one or more asymmetric centres and can therefore exist as enantiomers and possibly as diastereoisomers. It is to be understood that the present invention relates to the use of all such isomers and mixtures thereof.

The above compounds are only illustrative of the tachykinin antagonists which are currently under investigation. As this listing of groups of compounds is not meant to be comprehensive, the methods of the present invention may employ any tachykinin receptor antagonist, in particular a neurokinin-1 receptor antagonist and is not limited to any particular structural class of compound.

Suitable pharmaceutically acceptable salts of the tachykinin antagonists of use in the present invention include acid addition salts which may, for example, be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, phosphoric acid or sulphuric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also contemplates salts thereof, preferably non-toxic pharmaceutically acceptable salts thereof, such as the sodium, potassium and calcium salts thereof.

Certain of the above defined terms may occur more than once in the above formula and upon such occurrence each term shall be defined independently of the other. Similarly, the use of a particular variable within a noted structural formula is intended to be independent of the use of such variable within a different structural formula.

Full descriptions of the preparation of the tachykinin antagonists which are employed in the present invention may be found in the references cited herein.

The identification of a compound as a tachykinin antagonist, in particular, a neurokinin-1 receptor antagonist, and thus able to have utility in the present invention may be readily determined without undue experimentation by methodology well known in the art, such as the assays described as follows.

TACHYKININ ANTAGONISM ASSAY

The activity of a compound for antagonizing tachykinins, in particular substance P and neurokinin A may be identified in accordance with the following assays.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer suplemented with 0.625 mg/ml Herring sperm DNA at 300 V and 950 uF using the IBI GENEZAPPER (IBI). The transfected cells were incubated in CHO media [10% fetal calf serum, 100 U/ml pennicilin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}$I-substance P (125I-Sp, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific 125I-SP binding (approximately 50,000 to 200,000 cells). In the binding assay, 200 ul of cells were added to a tube containing 20 ul of 1.5 to 2.5 nM of $^{125}$I-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1 N HCl is added. Each well is sonicated at 4° C. and extracted with $CHCl_3$/methanol (1: 1). The aqueous phase is applied to a 1 ml Dowex AG 1×8 ion exchange column. The column is washed with 0.1 N formic acid followed by 0.025 M ammonium formate-0.1 N formic acid. The inositol monophosphate is eluted with 0.2 M ammonium formate-0.1 N formic acid and quantitated by beta counter.

For additional details regarding these assays see U.S. Pat. Nos. 5,494,886 and 5,525,712. The activity of the present compounds may also be demonstrated by the assay disclosed by Lei, et al., *British J. Pharmacol.*, 105, 261–262 (1992). In particular, the intrinsic tachykinin antagonist activity, especially the neurokinin-1 receptor antagonist activity, of a compound which may be employed in the present invention may be determined by the foregoing assays.

Suitable pharmaceutically acceptable salts of the tachykinin antagonists of use in the present invention include acid addition salts which may, for example, be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, phosphoric acid or sulphuric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also contemplates salts thereof, preferably non-toxic pharmaceutically acceptable salts thereof, such as the sodium, potassium and calcium salts thereof.

The tachyninin antagonist may be used alone or in conjunction with other agents which are known to be beneficial in altering circadian rhythms or in the enhancement of sleep efficiency. The tachykinin antagonist and the other agent may be coadministered, either in concomitant therapy or in a fixed combination, or they may be administered at separate times. For example, the tachykinin antagonist may be administered in conjunction with other compounds which are known in the art to be useful for suppressing or stimulating melatonin production including melatonergic agents, noradrenergic and serotonergic re-uptake blockers, alpha-1-noradrenergic agonists, monamine oxidase inhibitors, neuropeptide Y agonists or antagonists; neurokinin-1 agonists; substance P; beta-adrenergic blockers and benzodiazepines, such as atenolol; or with other compounds which are known in the art to be useful for stimulating melatonin production including tricyclic antidepressants and alpha-2-adrenergic antagonists; or with melatonin precursors such as tryptophan, 5-hydroxytryptophan, serotonin and N-acetylserotonin; as well as melatonin analogs, melatonin agonists and melatonin antagonists, or melatonin itself. In addition, the tachykinin antagonist may be administered in conjunction with other compounds which are known in the art to be useful for enhancing sleep quality and preventing and treating sleep disorders and sleep disturbances, including e.g., sedatives, hypnotics, anxiolytics, antipsychotics, antianxiety agents, minor tranquilizers, melatonin agonists and antagonists, melatonin, melatonergic agents, benzodiazepines, barbituates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, valproate, venlafaxine, zaleplon, zolazepam, zolpidem, and salts thereof, and combinations thereof, and the like.

The tachykinin antagonist may be administered in conjunction with the use of physical methods such as with light therapy or electrical stimulation. In particular, the tachykinin antagonist may be administered in conjunction with scheduling bright light administration, ordinary-intensity light exposure, or exposure to dim-light or darkness (or even sleep). In one embodiment of the present invention, the tachykinin antagonist is administered accompanied by having an individual wear dark or red goggles at the time of administration to provide additive effects of the treatment plus darkness. In another embodiment of the present invention, the individual wears dark goggles at times other than the time of tachykinin antagonist administration to avoid the occurrence of an external zeitgeber with respect to the phase shift resulting from the tachykinin antagonist. Similarly, bright light exposure can be used in conjunction with administration of a tachykinin antagonist.

Accordingly, the present invention further includes within its scope the use of a tachykinin antagonist, especially a neurokinin-1 receptor antagonist, alone or in combination with other agents, for altering circadian rhythms or for the prevention or treatment of sleep disorders and sleep disturbances in a mammal. The preferred mammal for purposes of this invention is human.

It will be appreciated to those skilled in the art that reference herein to treatment extends to prophylaxis (prevention) as well as the treatment of the noted diseases/disorders and symptoms.

Included within the scope of the present invention is the method of using a tachykinin antagonist for altering circadian rhythms or for enhancing and improving the quality of sleep. The tachykinin antagonist is useful in enhancing or improving sleep quality as well as preventing and treating sleep disorders and sleep disturbances in a mammal. In addition, the use of the tachykinin antagonist increases sleep efficiency and augments sleep maintenance. The tachykinin antagonist may further be used in a a method for preventing and treating sleep disorders and sleep disturbances in a mammal. The present invention further provides a pharmaceutical composition for altering circadian rhythms or for enhancing or improving sleep quality and increasing sleep efficiency and sleep maintenance.

The present method of using a tachykinin antagonist further provides the following: an increase in the value which is calculated from the time that a subject sleeps divided by the time that a subject is attempting to sleep; a decrease in sleep latency (the time it takes to fall asleep); a decrease in the number of awakenings during sleep; a decrease in the time spent awake following the initial onset of sleep; an increase in the total amount of sleep; an increase the amount and percentage of REM sleep; an increase in the duration and occurrence of REM sleep; a reduction in the fragmentation of REM sleep; an increase in the amount and percentage of slow-wave (i.e. stage 3 or 4) sleep; an increase in the amount and percentage of stage 2 sleep; a decrease in the number of awakenings, especially in the early morning; an increase in daytime alertness; and increased sleep maintenance; enhanced cognitive function; and increased memory retention.

The present invention is further useful for the prevention and treatment of sleep disorders and sleep disturbances including: sleep problems associated with insomnia, hypersomnia, sleep apnea, narcolepsy, nocturnal myoclonus, REM sleep interruptions, jet-lag, shift workers' sleep disturbances, dysomnias, night terror, insomnias associated with depression or with emotionalmood disorders, as well as sleep walking and enuresis, as well as sleep disorders which accompany aging, conditions associated with circadian rhythmicity, mental and physical disorders associated with travel across time zones and with rotating shift-work schedules, or syndromes such as fibromyalgia which are manifested by non-restorative sleep and muscle pain or sleep apnea which is associated with respiratory disturbances during sleep.

In addition, the present invention includes within its scope a pharmaceutical composition for enhancing and improving the quality of sleep comprising, as an active ingredient, at least one tachykinin antagonist in association with a pharmaceutical carrier or diluent.

The present invention further includes the use of a tachykinin antagonist in the manufacture of a medicament for achieving a circadian rhythm phase-shifting effect, alleviating a circadian rhythm disorder, blocking the phase-shifting effects of light, enhancing and improving the quality of sleep, or for the treatement of sleep disorders or sleep disturbances.

It will be known to those skilled in the art that there are numerous compounds now being used to affect circadian rhythms or to enhance and improve the quality of sleep. Combinations of these therapeutic agents some of which have also been mentioned herein with a tachykinin antagonist will bring additional, complementary, and often synergistic properties to enhance the desirable properties of these various therapeutic agents. In these combinations, the tachykinin antagonist and the therapeutic agents may be independently present in dose ranges from one one-hundredth to one times the dose levels which are effective when these compounds are used singly.

The tachykinin antagonist may be administered in combination with sedatives, hypnotics, anxiolytics, antipsychotics, antianxiety agents, minor tranquilizers, melatonin agonists and antagonists, melatonergic agents, benzodiazepines, barbituates, 5HT-2 antagonists, and the like, or the tachykinin antagonist may be administered in conjunction with the use of physical methods such as with light therapy or electrical stimulation. For example, to alter circadian rhythmicity or to enhance and improve the quality of sleep a tachykinin antagonist may be given in combination with such compounds as: adinazolam, allobarbital, alonimid, alprazolam, amitriptyline, amobarbital, amoxapine, bentazepam, benzoctarmine, brotizolam, bupropion, busprione, butabarbital, butalbital, capuride, carbocloral, chloral betaine, chloral hydrate, chlordiazepoxide, clomipramine, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, valproate, venlafaxine, zaleplon, zolazepam, zolpidem, and salts thereof, and combinations thereof, and the like, as well as admixtures and combinations thereof.

Typically, the individual daily dosages for these combinations may range from about one-fifth of the minimally recommended clinical dosages to the maximum recommended levels for the entities when they are given singly.

To illustrate these combinations, a tachykinin antagonist effective clinically at a given daily dose range may be effectively combined, at levels which are equal or less than the daily dose range, with the following compounds at the indicated per day dose range: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, as well as admixtures and combinations thereof. It will be readily apparent to one skilled in the art that the tachykinin antagonist may be employed with other agents to alter circadian rhythms or to control sleep disorders and sleep disturbances in depressed patients and/or provide benefit in the prevention or treatment of sleep disorders and sleep disturbances.

Naturally, these dose ranges may be adjusted on a unit basis as necessary to permit divided daily dosage and, as noted above, the dose will vary depending on the nature and severity of the disease, weight of patient, special diets and other factors.

These combinations may be formulated into pharmaceutical compositions as known in the art and as discussed below. A tachykinin antagonist may be administered alone or in combination by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. In the case of capsules, tablets and pills, the dosage forms may also comprise buffering agents.

When the dosage unitform is a capsule, it may contain, in addition to materials of the above type, a liquid carrier such as fatty oil. Various other materials may be present as coatings or to otherwise modify the physical form of the dosage unit. Tablets and pills can additionally be prepared with enteric coatings and tablets may be coated with shellac, sugar or both.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents. A syrup or elixir may contain the active compound, sucrose as a sweetening agent, methyl and propyl parabens as preservatives, a dye and a flavoring such as cherry or orange flavor.

Preparations according to this invention for parenteral administration include sterile aqueous or non-aqueous solutions, suspensions, or emulsions. Sterile compositions for injection may be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like may be incorporated as required. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use. Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. As will be readily apparent to one skilled in the art, the effect of a tachykinin antagonist which induces a phase shift in a central circadian pacemaker may be dependent on both the ambient and circadian time of administration. The same compound may induce a phase advance, a phase delay or have minor effect on a particular circadian rhythm depending on the circadian time of administration. The dose will vary from patient to patient depending upon the nature and severity of disease, the patient's weight, special diets then being followed by a patient, concurrent medication, the intrinsic tachykinin antagonist activity of the compound, the bioavailability upon oral administration of the compound and other factors which those skilled in the art will recognize.

In the treatment of a condition in accordance with the present invention, an appropriate dosage level will generally be about 0.01 $\mu$g to 50 mg per kg patient body weight per day which may be administered in single or multiple doses. Preferably, the dosage level will be about 0.1 $\mu$g to about 25 mg/kg per day; more preferably about 0.5 $\mu$g to about 10 mg/kg per day. For example, for achieving a circadian rhythm phase-shifting effect, resetting the internal circadian clock, shortening the time of reintrainment of circadian rhythms, alleviating a circadian rhythm disorder or enhancing the quality of sleep, a suitable dosage level is about 0.1 $\mu$g to 25 mg/kg per day, preferably about 0.5 $\mu$g to 10 mg/kg per day, and especially about 1 $\mu$g to 5 mg/kg per day. In larger mammals, for example humans, a typical indicated dose is about 300 $\mu$g to 400 mg orally. A compound may be administered on a regimen of several times per day, for example 1 to 4 times per day, preferably once or twice per day. When using an injectable formulation, a suitable dosage level is about 0.1 $\mu$g to 10 mg/kg per day, preferably about 0.5 $\mu$g to 5 mg/kg per day, and especially about 1 $\mu$g to 1 mg/kg per day. In larger mammals, for example humans, a typical indicated dose is about 100 $\mu$g to 100 mg i.v. A compound may be administered on a regimen of several times per day, for example 1 to 4 times per day, preferably once or twice per day.

Pharmaceutical compositions of the present invention may be provided in a solid dosage formulation preferably comprising about 100 $\mu$g to 500 mg active ingredient, more preferably comprising about 100 $\mu$g to 250 mg active ingredient. The pharmaceutical composition is preferably provided in a solid dosage formulation comprising about 100 $\mu$g, 1 mg, 5 mg, 10 mg, 25 mg, 50 mg, 100 mg, 200 mg or 250 mg active ingredient.

The following examples are provided for the purpose of further illustration only and are not intended to be limitations on the disclosed invention.

EXAMPLE 1

Double-Blind, Placebo-Controlled Study to Determine the Effect of a Substance P Antagonist on Light-Induced Melatonin Suppression in Healthy Young Men The purpose of this study is to evaluate the effects of a substance P antagonist on circadian rhythms in humans by examining the amount of light-induced melatonin suppression in subjects treated with placebo or the substance P (NK1) antagonist. If a substance P antagonist is able to alter the amount of light-induced melatonin suppression and so influence circadian rhythms, it may be a useful agent, e.g., for treating jet lag, shift workers, seasonal affective disorder, and sleep disorders in the elderly.

This study is a double-blind, randomized, placebo-controlled, crossover, single-center study in healthy young men. After completing the screening visit, subjects follow a regular sleep/wake schedule for 2 weeks at home while wearing an actigraphy monitor in order to confirm their compliance. After the 2-week period, subjects begin the in-laboratory portion of the study, during which they will spend a baseline day in constant routine (CR) conditions, a night of sleep in the laboratory, followed by another CR day and night, during which time subjects will not go to sleep, but have a melatonin suppression test, followed by a day of recovery when subjects sleep and then are discharged before nighttime. Two hours before their typical bedtime on Day 2, subjects receive orally either the substance P antagonist 2-(R)-(1-(R)-(3,5-bis(trifluoromethyl)phenyl)-ethoxy)-3-(S)-(4-fluorophenyl)-4-(3-(5-oxo-1H,4H-1,2,4-triazolo) methylmorpholine or placebo. Four hours later, 2 hours after their typical bedtime, subjects are exposed to a 5-hour pulse of moderately bright light (300–900 lux). Following the light exposure, subjects stay in CR conditions for another 5 hours, be allowed to sleep, and then leave the laboratory. Blood sampling is performed on subjects throughout the in-laboratory visit in order to collect samples for melatonin assays. Subjects remain at home for a 3- to 8-week washout period before returning for the second part of the study. During the last 2 weeks before the subjects come back into the laboratory, they follow a regular sleep/wake schedule for 2 weeks at home with actigraphic monitoring in order to confirm their compliance. Subjects then return to the laboratory to follow the same 3-day protocol but they receive the opposite drug treatment (i.e substance P antagonist or placebo). The pnmary response, suppression of melatonin, is assessed by calculating the percent change from baseline in the melatonin plasma during the 5-hour light pulse. The baseline value is defined as the melatonin plasma AUC of the corresponding 5 hours which occurred 24 hours earlier.

The results of the foregoing study indicate that the administration of a substance P antagonist can induce a change in the phase of the free-running circadian clock and block the phase-shifting effects of light on the mammalian circadian clock.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for alleviating a circadian rhythm disorder in a mammal in need thereof which comprises administering to the mammal an effective amount of a CNS-penetrating neurokinin-1 receptor antagonist.

2. A method for the prevention or treatment of a circadian rhythm disorder in a human in need thereof which disorder is selected from the group consisting of: time-zone change (jet-lag) syndrome, shift-work sleep disorder, delayed sleep-phase syndromes, advanced sleep-phase syndrome, and non-24-hour sleep-wake disorder which comprises administering to the human an effective amount of a CNS-penetrating neurokinin-1 receptor antagonist.

3. A method for alleviating the effects of jet lag in a human in need thereof which comprises administering to the human an effective amount of a CNS-penetrating neurokinin-1 receptor antagonist.

4. A method for alleviating the effects of shift-work sleep disorder in a human in need thereof which comprises administering to the human an effective amount of a CNS-penetrating neurokinin-1 receptor antagonist.

5. The method of claim 1 wherein the mammal is a human.

6. The method of claim 5 wherein the neurokinin-1 receptor antagonist is an orally active neurokinin-1 receptor antagonist.

7. The method of claim 6 wherein the neurokinin-1 receptor antagonist is a non-peptidal neurokinin-1 receptor antagonist.

8. The method of claim 6 wherein the neurokinin-1 receptor antagonist is administered in conjunction with melatonin or a compound which suppresses or stimulates melatonin production.

9. The method of claim 6 wherein the neurokinin-1 receptor antagonistis administered in conjunction with light therapy.

10. The method of claim 1 wherein the neurokinin-1 receptor antagonist is selected from group consisting of:
(2R*,4S*)-2-benzyl-1-(3,5-dimethylbenzoyl)-N-(4-quinolinylmethyl)-4-piperidineamine;
[2-methoxy-5-(5-trifluoromethyl-tetrazol-1-yl)-benzyl]-(2S-phenyl-piperidin-3S-yl)-amine;
[5-(5-methyl-tetrazol-1-yl)-benzofuran-7-ylmethyl]-(2S-phenyl-piperidin-3S-yl)-amine;
2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methylmorpholine;
2-(R)-(1-(R)-(3,5-bis(trifluoromethyl)phenyl)ethoxy)-4-((dimethylamino-methyl)-1,2,3-triazol-4-yl)methyl)-3-(S)-(4-fluorophenyl)morpholine;
2-(R)-(1-(R)-(3,5-bis(trifluoromethyl)phenyl)ethoxy)-3-(S)-(4-fluoro)-phenyl-4-(3-(1-monophosphoryl-5-oxo-1H-1,2,4-triazolo)methyl)morpholine;
(2S,3S)-cis-3-(2-methoxybenzylamino)-2-phenylpiperidine;
(3aS,4S,7aS)-7,7-diphenyl-4-(2-methoxyphenyl)-2-[(2S)-(2-methoxyphenyl)propionyl]perhydroisoindol-4-ol;
(+) 1-[2-[3-(3,4-dichlorophenyl)-1-[(3-isopropoxyphenyl)-acetyl]-3-piperidinyl]ethyl]-4-phenyl-1-azabicyclo[2,2,2]octane;
and pharmaceutically acceptable salts thereof.

11. The method of claim 2 wherein the neurokinin-1 receptor antagonist is an orally active neurokinin-1 receptor antagonist.

12. The method of claim 11 wherein the neurokinin-1 receptor antagonist is a non-peptidal neurokinin-1 receptor antagonist.

13. The method of claim 2 wherein the neurokinin-1 receptor antagonist is administered in conjunction with melatonin or a compound which suppresses or stimulates melatonin production.

14. The method of claim 2 wherein the neurokinin-1 receptor antagonist is selected from group consisting of:
(2R*,4S*)-2-benzyl-1-(3,5-dimethylbenzoyl)-N-(4-quinolinylmethyl)-4-piperidineamine;
[2-methoxy-5-(5-trifluoromethyl-tetrazol-1-yl)-benzyl]-(2S-phenyl-piperidin-3S-yl)-amine;
[5-(5-methyl-tetrazol-1-yl)-benzofuran-7-ylmethyl]-(2S-phenyl-piperidin-3S-yl)-amine;
2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl-morpholine;
2-(R)-(1-(R)-(3,5-bis(trifluoromethyl)phenyl)ethoxy)-4-((dimethylamino-methyl)-1,2,3-triazol-4-yl)methyl)-3-(S)-(4-fluorophenyl)morpholine;
2-(R)-(1-(R)-(3,5-bis(trifluoromethyl)phenyl)ethoxy)-3-(S)-(4-fluoro)-phenyl-4-(3-(1-monophosphoryl-5-oxo-1H-1,2,4-triazolo)methyl)morpholine;
(2S,3S)-cis-3-(2-methoxybenzylamino)-2-phenylpiperidine;

(3aS,4S,7aS)-7,7-diphenyl-4-(2-methoxyphenyl)-2-[(2S)-(2-methoxyphenyl)propionyl]perhydroisoindol-4-ol;

(+) 1-[2-[3-(3,4-dichlorophenyl)-1-[(3-isopropoxyphenyl)-acetyl]-3-piperidinyl]ethyl]-4-phenyl-1-azabicylo[2,2,2]octane;

and pharmaceutically acceptable salts thereof.

15. The method of claim 3 wherein the neurokinin-1 receptor antagonist is a non-peptidal neurokinin-1 receptor antagonist.

16. The method of claim 3 wherein the neurokinin-1 receptor antagonist is administered in conjunction with melatonin or a compound which suppresses or stimulates melatonin production.

17. The method of claim 3 wherein the neurokinin-1 receptor antagonist is selected from group consisting of:

(2R*,4S*)-2-benzyl-1-(3,5-dimethylbenzoyl)-N-(4-quinolinylmethyl)-4-piperidineamine;

[2-methoxy-5-(5-trifluoromethyl-tetrazol-1-yl)-benzyl]-(2S-phenyl-piperidin-3S-yl)-amine;

[5-(5-methyl-tetrazol-1-yl)-benzofuran-7-ylmethyl]-(2S-phenyl-piperidin-3S-yl)-amino;

2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl-morpholine;

2-(R)-(1-(R)-(3,5-bis(trifluoromethyl)phenyl)ethoxy)-4-((dimethylamino-methyl)-1,2,3-triazol-4-yl)methyl)-3-(S)-(4-fluorophenyl)morpholine;

2-(R)-(1-(R)-(3,5-bis(trifluoromethyl)phenyl)ethoxy)-3-(S)-(4-fluoro)-phenyl-4-(3-(1-monophosphoryl-5-oxo-1H-1,2,4-triazolo)methyl)morpholine;

(2S,3S)-cis-3-(2-methoxybenzylamino)-2-phenylpiperidine;

(3aS,4S,7aS)-7,7-diphenyl-4-(2-methoxyphenyl)-2-[(2S)-(2-methoxyphenyl)propionyl]perhydroisoindol-4-ol;

(+) 1-[2-[3-(3,4-dichlorophenyl)-1-[(3-isopropoxyphenyl)-acetyl]-3-piperidinyl]ethyl]-4-phenyl-1-azabicyclo[2,2,2]octane;

and pharmaceutically acceptable salts thereof.

18. The method of claim 4 wherein the neurokinin-1 receptor antagonist is a non-peptidalneurokinin-1 receptor antagonist.

19. The method of claim 4 wherein the neurokinin-1 receptor antagonist is administered in conjunction with melatonin or a compound which suppresses or stimulates melatonin production.

20. The method of claim 4 wherein the neurokinin-1 receptor antagonist is selected from group consisting of:

(2R*,4S*)-2-benzyl-1-(3,5-dimethylbenzoyl)-N-(4-quinolinylmethyl)-4-piperidineamine;

[2-methoxy-5-(5-trifluoromethyl-tetrazol-1-yl)-benzyl]-(2S-phenyl-piperidin-3S-yl)-amine;

[5-(5-methyl-tetrazol-1-yl)-benzofuran-7-ylmethyl]-(2S-phenyl-piperidin-3S-yl)-amine;

2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl-morpholine;

2-(R)-(1-(R)-(3,5-bis(trifluoromethyl)phenyl)ethoxy)-4-((dimethylamino-methyl)-1,2,3-triazol-4-yl)methyl)-3-(S)-(4-fluorophenyl)morpholine;

2-(R)-(1-(R)-(3,5-bis(trifluoromethyl)phenyl)ethoxy)-3-(S)-(4-fluoro)-phenyl-4-(3-(1-monophosphoryl-5-oxo-1H-1,2,4-triazolo)methyl)morpholine;

(2S,3S)-cis-3-(2-methoxybenzylamino)-2-phenylpiperidine;

(3aS,4S,7aS)-7,7-diphenyl-4-(2-methoxyphenyl)-2-[(2S)-(2-methoxyphenyl)propionyl]perhydroisoindol-4-ol;

(+) 1-[2-[3-(3,4-dichlorophenyl)-1-[(3-isopropoxyphenyl)-acetyl]-3-piperidinyl]ethyl]-4-phenyl-1-azabicyclo[2,2,2]octane;

and pharmaceutically acceptable salts thereof.

* * * * *